US006214795B1

(12) United States Patent
Benjamin et al.

(10) Patent No.: US 6,214,795 B1
(45) Date of Patent: *Apr. 10, 2001

(54) PEPTIDE COMPOUNDS USEFUL FOR MODULATING FGF RECEPTOR ACTIVITY

(75) Inventors: Howard Benjamin; Ling Chai, both of Lexington; Mark A. Findeis, Cambridge; William Goodwin, Melrose; Arvind Hundal, Brighton; David I. Israel, Concord; Michael Kelley, Arlington; Martin P. Keough, Abington; Kuanghui Lu, Cambridge; Farah Natoli, Quincy; Alicia Peticolas, Watertown; Ethan R. Signer, Cambridge; Malcolm L. Gefter, Lincoln, all of MA (US)

(73) Assignee: Praecis Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/747,599

(22) Filed: Nov. 12, 1996

(51) Int. Cl.$^7$ .............................. C07K 7/00; A61K 38/08; A61K 38/10; A61K 38/16
(52) U.S. Cl. ................................ 514/12; 514/13; 514/14; 514/15; 530/324; 530/325; 530/326; 530/327
(58) Field of Search .......................... 530/300, 324–328; 514/2, 12, 13, 14, 15

(56) References Cited

U.S. PATENT DOCUMENTS 5,288,855  2/1994  Bergonzoni et al. ................. 530/399

FOREIGN PATENT DOCUMENTS

| 246753 | 1/1989 | (EP) . |
| 298723 | 3/1990 | (EP) . |
| 0 529 076 B1 | 6/1995 | (EP) . |
| WO 9002800 | 11/1987 | (WO) . |
| WO 91/00916 | 1/1991 | (WO) . |
| WO 92/00999 | 1/1992 | (WO) . |
| WO 92/13958 | 8/1992 | (WO) . |

OTHER PUBLICATIONS

Champion–Arnaud P. et al. (1991) "Multiple mRNAs code for proteins related to the BEK fibroblast growth factor receptor" *Oncogene* 6:979–987.

Crumley G. et al. (1991) "High–affinity binding and activation of a truncated FGF receptor by both aFGF and bFGF" *Oncogene* 6:2255–2262.

Dionne C.A. et al. (1990) "Cloning and expression of two distinct high–affinity receptors cross–reacting with acidic and basic fibroblast growth factors" *The EMBO Journal* 9(9);2685–2692.

Eisemann A. et al. (1991) Alternative splicing generates at least five different isoforms of the human basic–FGF receptor *Oncogene* 6:1195–1202.

Gospodarowicz D. et al. (1986) "Molecular and biological characterization of fibroblast growth factor, an angiogenic factor which also controls the proliferation and differentiation of mesoderm and neuroectoderm derived cells" *Cell Differentiation* 19:1–17.

Hou J. et al. (1991) "Fibroblast Growth Factor Receptors from Liver Vary in Three Structural Domains" Abstract, p. 665–668.

Johnson D.E. et al. (1990) "Diverse Forms of a Receptor for Acidic and Basic Fibroblast Growth Factors" *Molecular and Cellular Biology* 10(9):4728–4736.

Lee P.L. et al. (1989) "Purification and Complementary DNA Cloning of a Receptor for Basic Fibroblast Growth Factor" Abstract, p. 57–60.

Werner S. et al. (1992) "Differential Splicing in the Extracellular Region of Fibroblast Growth Factor Receptor 1 Generates Receptor Variants with Different Ligand–Binding Specificities" *Molecular and Cellular Biology* 12(1):82–88.

Primary Examiner—Christine Saoud
(74) Attorney, Agent, or Firm—Lahive & Cockfield, LLP; Giulio A. DeConti, Jr.; Catherine J. Kara

(57) ABSTRACT

This invention provides peptide compounds that bind to either a fibroblast growth factor (FGF) or a fibroblast growth factor receptor (FGFR) and, accordingly, are useful for modulating FGFR activity. Preferably, the FGFR is FGFR2-IIIC. Preferably, the FGF is basic FGF. Preferably the peptide compound comprises an amino acid sequence: (Y/F)-(L/F/I)-(R/D/E/S/Y/G)-(Q/L/Y)-Y-(M/L/K/R)-(L/M/D/E/N/S)-(R/L/S/T)-(L/F/M/V) (SEQ ID NO: 1). The invention further comprises pharmaceutical compositions comprising the peptide compounds of the invention and a pharmaceutically acceptable carrier. The invention still further provides methods of modulating FGFR activity using the peptide compounds of the invention.

14 Claims, 6 Drawing Sheets

PEPTIDE COMPOUNDS USEFUL FOR MODULATING FGF RECEPTOR ACTIVITY

BACKGROUND OF THE INVENTION

The fibroblast growth factor (FGF) family consists of closely related polypeptide mitogens. This family includes at least seven members based on amino acid sequence homologies: basic FGF (Esch et al. (1985) *Proc. Natl. Acad. Sci. USA* 82:6507–6511; Abraham et al. (1986) *Science* 233:545–548; Abraham et al. (1986) *EMBO J.* 5:2523–2528; Kurokawa et al. (1987) *FEBS Lett.* 213:189–194), acidic FGF (Gimenez-Gallago et al. (1985) *Science* 230:1385–1388; Thomas et al. (1985) *Proc. Natl. Acad. Sci. USA* 82:6409–6413; Jaye et al. (1986) *Science* 233:543–545), int-2 (Moore et al. (1986) *EMBO J.* 5:919–924), hst (Kaposi sarcoma FGF) (Taira et al. (1987) *Proc. Natl. Acad. Sci. USA* 84:2980–2984; Bovi et al. (1987) *Cell* 50:729–737), FGF-5 (Zhan et al. (1988) *Mol. Cell. Biol.* 8:3487–3495), FGF-6 (Marics et al. (1989) *Oncogene* 4:335–340) and keratinocyte growth factor (KGF)(Finch et al. (1989) *Science* 245:752–755; Rubin et al. (1989) *Proc. Natl. Acad. Sci. USA* 86:802–806).

The pleiotropic effects of the FGF family members include proliferative activity for a wide variety of cells, neurotrophic activity and angiogenic activity (Gospodarowicz et al. (1986) *Cell. Differ.* 19:1–17; Morrison et al. (1986) *Proc. Natl. Acad. Sci. USA* 83:7537–7541; Walicke et al. (1986) *Proc. Natl. Acad. Sci. USA* 83:3012–3016; Folkman and Klagsbrun (1987) *Science* 235:442–447; Thomas (1987) *FASEB J.* 1:434–440; Anderson et al. (1988) *Nature* 332:360–361; Burgess and Maciag (1989) *Annu. Rev. Biochem.* 58:575–606). The FGFs also have the ability to influence the differentiation of a variety of cell types, exhibiting both differentiation-inducing and differentiation-inhibiting effects (Linkhart et al. (1981) *Dev. Biol.* 86:19–30; Serrero and Khoo (1982) *Anal. Biochem.* 120:351–359; Broad and Ham (1983) *Eur. J. Biochem.* 135:33–39; Lathrop et al. (1985) *J. Cell. Biol.* 100:1540–1547; Togari et al. (1985) *J. Neurosci.* 5:307–316; Wagner and D'Amore (1986) *J. Cell. Biol.* 103:1363–1367; Anderson et al. (1988) *Nature* 332:360–361). FGFs are also thought to play an important role in embryonal development (Kimelman and Kirschner (1987) *Cell* 51:869–877; Slack et al. (1987) *Nature* 326:197–200; Kimelman et al. (1988) *Science* 242:1053–1056; Amaya et al. (1991) *Cell* 66:257–270).

The FGFs mediate their effects by binding to high affinity cell surface receptors (reviewed in Johnson and Williams (1992) *Adv. Cancer Res.* 60:1–41). Four distinct FGF receptors have been identified: FGFR1 (also known was Flg, bFGFR, Cek1 or N-bFGFR) (Lee et al. (1989) *Science* 245:57–60; Dionne et al. (1990) *EMBO J.* 9:2685–2692; Johnson et al. (1990) *Mol. Cell. Biol.* 10:4728–4736; Eisemann et al. (1991) *Oncogene* 6:1195–1202; Hou et al. (1991) *Science* 251:665–668), FGFR2 (also known as Bek, Cek3, K-sam, TK14, TK25 or KGFR) (Dionne et al. (1990) *EMBO J.* 9:2685–2692; Hattori et al. (1990) *Proc. Natl. Acad. Sci. USA* 87:5983–5987; Miki et al. (1991) *Science* 251:72–75; Saiki et al. (1988) *Science* 239:487–491; Pasquale (1990) *Proc. Natl. Acad. Sci. USA* 87:5812–5816; Houssaint et al. (1990) *Proc. Natl. Acad. Sci. USA* 87:8180–8184; Champion-Arnaud et al. (1991) *Oncogene* 6:979–987; Crumley et al. (1991) *Oncogene* 6:2255–2262; Raz et al. (1991) *Oncogene* 6:753–760; Sato et al. (1991) *Oncogene* 6:1279–1283), FGFR3 (also known as Cek2) (Keegan et al. (1991) *Proc. Natl. Acad. Sci. USA* 88:1095–1099) and FGFR4 (Partanen et al. (1991) *EMBO J.* 10:1347–1354).

Structurally, the FGF receptors comprise an amino terminal signal peptide, three extracellular immunoglobulin-like domains (Ig domain I, Ig domain II, Ig domain III), with an acidic region between Ig domains I and II (the "acidic box" domain), a transmembrane region, and intracellular kinase domains (Johnson and Williams (1992) *Adv. Cancer Res.* 60:1–41). Variant forms of FGF receptors are generated by alternative mRNA splicing (Champion-Arnaud et al. (1991) *Oncogene* 6:979–987; Johnson et al. (1991) *Mol. Cell. Biol.* 11:4627–4634; Johnson and Williams (1992) *Adv. Cancer Res.* 60:1–41). Binding studies have demonstrated that multiple members of the FGF family can bind to the same receptor species (Dionne et al. (1990) *EMBO J.* 9:2685–2692; Johnson et al. (1990) *Mol. Cell. Biol.* 10:4728–4736; Mansukhani et al. (1990) *Proc. Natl. Acad. Sci. USA* 87:4378–4382; Keegan et al. (1991) *Proc. Natl. Acad. Sci. USA* 88:1095–1099). Alternative splice variants, particularly involving Ig domain III, are thought to be important in determining the ligand binding specificity of receptor species (Werner (1992) *Mol. Cell. Biol.* 12:82–88; Crumley et al. (1991) *Oncogene* 6:2255–2262). Moreover, analogous splice variants from different FGFR genes have been shown to encode receptor forms with different ligand binding specificities (Dionne et al. (1990) *EMBO J.* 9:2685–2692; Johnson et al. (1990) *Mol. Cell. Biol.* 10:4728–4736; Mansukhani et al. (1990) *Proc. Natl. Acad. Sci. USA* 87:4378–4382).

Given the role of FGF family members in a variety of biological processes, compounds that modulate FGF receptor activity would be advantageous. Certain retro-peptides have been described as FGF receptor blocking peptides (PCT Publication No. WO 92/13958). Moreover, soluble forms of FGF receptors, comprising the extracellular domains, have been described (U.S. Pat. No. 5,288,855 by Bergonzoni et al.; PCT Publication No. WO 91/00916; PCT Publication WO 92/00999; European Patent 529 076 B1). Additional compounds for modulating FGF receptor activity are still needed.

SUMMARY OF THE INVENTION

This invention pertains to peptide compounds, pharmaceutical compositions comprising these peptide compounds and methods of using these peptide compounds. The peptide compounds of the invention bind either a fibroblast growth factor (FGF) or a fibroblast growth factor receptor (FGFR) (preferably, FGFR2-IIIC). Accordingly, the peptide compounds of the invention are useful as modulators of FGFR activity. A peptide compound of the invention may be an agonist or an antagonist of FGFR activity.

In a preferred embodiment, a peptide compound of the invention is based on the consensus amino acid sequence: (Y/F)-(L/F/I)-(R/D/E/S/Y/G)-(Q/L/Y)-Y-(M/L/K/R)-(L/M/D/E/N/S)-(R/L/S/T)-(L/F/M/V) (SEQ ID NO: 1). Accordingly, a peptide compound of the invention can comprise an amino acid sequence:

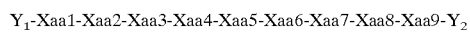

$Y_1$-Xaa1-Xaa2-Xaa3-Xaa4-Xaa5-Xaa6-Xaa7-Xaa8-Xaa9-$Y_2$ wherein:

$Y_1$ is hydrogen, an amino-derivative group or a peptidic structure having a formula $(Xaa)_a$ wherein Xaa is any amino acid structure and a is an integer from 1–15 inclusive;

$Y_2$ is hydrogen, a carboxy-derivative group or a peptidic structure having a formula $(Xaa)_b$ wherein Xaa is any amino acid structure and b is an integer from 1–15 inclusive;

Xaa1 is a tyrosine structure or a phenylalanine structure;

Xaa2 is a leucine structure, a phenylalanine structure or isoleucine structure;

Xaa3 is an arginine structure, an aspartic acid structure, a glutamic acid structure, a serine structure, a tyrosine structure or a glutamine structure;

Xaa4 is glutamine structure, a leucine structure or a tyrosine structure;

Xaa5 is a tyrosine structure;

Xaa6 is a methionine structure, a leucine structure, a lysine structure or an arginine structure;

Xaa7 is a leucine structure, a methionine structure, an aspartic acid structure, a glutamic acid structure, an asparagine structure or a serine structure;

Xaa8 is an arginine structure, a leucine structure, a serine structure or a threonine structure; and Xaa9 is leucine, phenylalanine structure, a methionine structure or a valine structure.

The peptide compounds of the invention can be formulated into pharmaceutical compositions, preferably comprising a peptide compound and a pharmaceutically acceptable carrier.

The peptide compounds of the invention can be used to modulate FGFR activity in a cell by contacting a cell expressing the FGFR with the peptide compound such that FGFR activity in the cell is modulated. In the modulatory methods of the invention, the peptide compound can be contacted with cell expressing FGFR in vitro or, alternatively, the peptide compound can be administered to a subject such that the peptide compound is contacted with a cell expressing FGFR in vivo. For peptide compounds that bind an FGF, the method can comprise contacting the cell with a peptide compound of the invention in the presence of FGF.

DETAILED DESCRIPTION OF THE INVENTION

Figure 1:
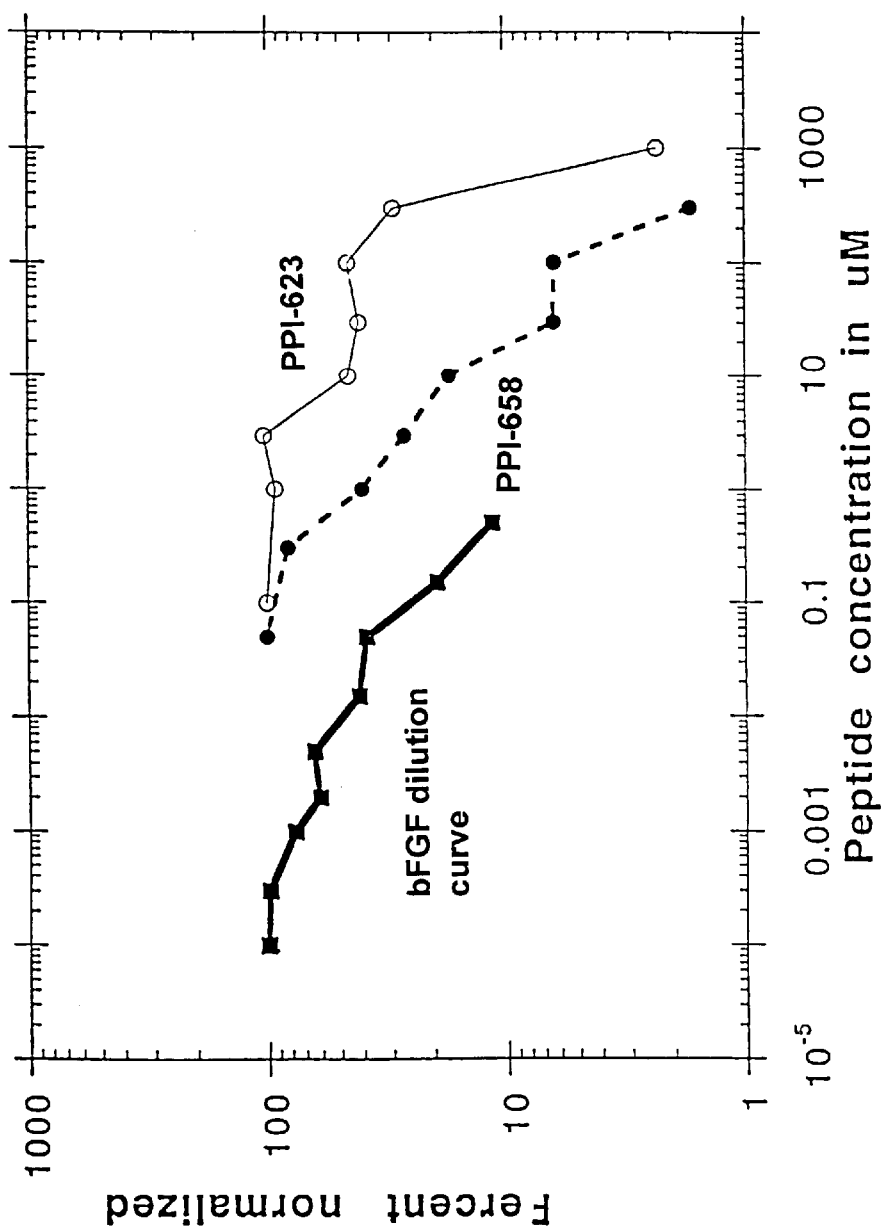
FIG. 1 is a graph depicting the effect of unlabeled bFGF, compound 623 or compound 658 on $^{125}$I-bFGF binding to soluble biotinylated FGF receptor.

This invention pertains to peptide compounds capable of binding a fibroblast growth factor (FGF) or a fibroblast growth factor receptor (FGFR), pharmaceutical compositions comprising the peptide compounds of the invention and methods of using the peptide compounds to modulate FGFR activity.

In a preferred embodiment, a peptide compound of the invention binds FGFR2-IIIC. As used herein, the term "FGFR2-IIIC" is intended to refer the exon IIIC splice variant of the FGFR2 (Bek) receptor family, as disclosed in Dionne et al. (1990) *EMBO J.* 9:2685–2692; Pasquale (1990) *Proc. Natl. Acad. Sci. USA* 87:5812–5816; Houssaint et al. (1990) *Proc. Natl. Acad. Sci. USA* 87:8180–8184; Champion-Arnaud et al. (1991) *Oncogene* 6:979–987; and Raz et al. (1991) *Oncogene* 6:753–760, or mammalian homologues thereof.

In another preferred embodiment, a peptide compound of the invention binds basic FGF (bFGF). As used herein, the term "basic FGF" is intended to refer to the growth factor as disclosed in Esch et al. (1985) *Proc. Natl. Acad. Sci. USA* 82:6507–6511; Abraham et al. (1986) *Science* 233:545–548; Abraham et al. (1986) *EMBO J.* 5:2523–2528; and Kurokawa et al. (1987) *FEBS Lett.* 213:189–194, or mammalian homologues thereof.

Various aspects of the invention are discussed further in the following subsections. Standard three-letter and one-letter abbreviations for amino acids are used throughout the application.

I. Peptide Compounds

In a preferred embodiment, a peptide compound of the invention comprises a consensus amino acid sequence: (Y/F)-(L/F/I)-(R/D/E/S/Y/G)-(Q/L/Y)-Y-(M/L/K/R)-(L/M/D/E/N/S)-(R/L/S/T)-(L/F/M/V) (SEQ ID NO: 1). Moreover, longer peptides encompassing this amino acid sequence, as well as peptide derivatives, peptide analogues and peptidomimetics of this amino acid sequence are encompassed by the invention. Accordingly, a peptide compound of the invention can comprise an amino acid sequence:

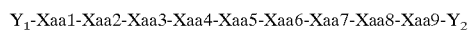

$Y_1$-Xaa1-Xaa2-Xaa3-Xaa4-Xaa5-Xaa6-Xaa7-Xaa8-Xaa9-$Y_2$ wherein:

$Y_1$ is hydrogen, an amino-derivative group or a peptidic structure having a formula $(Xaa)_a$ wherein Xaa is any amino acid structure and a is an integer from 1–15 inclusive;

$Y_2$ is hydrogen, a carboxy-derivative group or a peptidic structure having a formula $(Xaa)_b$ wherein Xaa is any amino acid structure and b is an integer from 1–15 inclusive;

Xaa1 is a tyrosine structure or a phenylalanine structure;

Xaa2 is a leucine structure, a phenylalanine structure or isoleucine structure;

Xaa3 is an arginine structure, an aspartic acid structure, a glutamic acid structure, a serine structure, a tyrosine structure or a glutamine structure;

Xaa4 is glutamine structure, a leucine structure or a tyrosine structure;

Xaa5 is a tyrosine structure;

Xaa6 is a methionine structure, a leucine structure, a lysine structure or an arginine structure;

Xaa7 is a leucine structure, a methionine structure, an aspartic acid structure, a glutamic acid structure, an asparagine structure or a serine structure;

Xaa8 is an arginine structure, a leucine structure, a serine structure or a threonine structure; and Xaa9 is leucine, phenylalanine structure, a methionine structure or a valine structure.

In a preferred embodiment, Xaa1 is a tyrosine structure or a phenylalanine structure, Xaa2 is a leucine structure or a phenylalanine structure, Xaa3 is an arginine structure, Xaa4 is a glutamine structure or a leucine structure, Xaa5 is a tyrosine structure, Xaa6 is a methionine structure, Xaa7 is a leucine structure, Xaa8 is an arginine structure and Xaa9 is a leucine structure.

As used herein, the terms "peptide compound" and "peptidic structure" are intended to include peptides comprised of naturally-occurring L-amino acids, as well as peptide derivatives, peptide analogues and peptide mimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide (e.g., the ability to bind an FGF or FGFR). Approaches to designing peptide analogues, derivatives and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages).

As used herein an "analogue" of a compound X refers to a compound which retains chemical structures of X necessary for functional activity of X yet which also contains certain chemical structures which differ from X. An examples of an analogue of a naturally-occurring peptide is a peptides which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937–1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942).

Other possible modifications include an N-alkyl (or aryl) substitution (ψ[CONR]), backbone crosslinking to construct lactams and other cyclic structures, substitution of all D-amino acids for all L-amino acids within the compound ("inverso" compounds) or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al. "*Perspectives in Peptide Chemistry*" pp. 283–294 (1981). See also U.S. Pat. No. 4,522,752 by Sisto for further description of "retro-inverso" peptides. Other derivatives include C-terminal hydroxymethyl derivatives, O-modified derivatives (e.g., C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound (e.g., the ability to bind an FGF or an FGFR). For example, the termr "phenylalanine structure" is intended to include phenylalanine as well as pyridylalanine and homophenylalanine. The term "leucine structure" is intended to include leucine, as well as substitution with valine or other natural or non-natural amino acid having an aliphatic side chain, such as norleucine.

The amino- and/or carboxy-terminus of the peptide compounds of the invention can be unmodified (ie., $Y_1$ and/or $Y_2$ can be, independently) hydrogen. Alternatively, the amino- and/or carboxy-terminus of the peptide compound can be modified with a derivative group. Amino-derivative groups which can be present at the N-terminus of a peptide compound (i.e., can be $Y_1$) include acetyl, aryl, aralkyl, acyl, epoxysuccinyl and cholesteryl groups. Carboxy-derivative groups which can be present at the C-terminus of a peptide compound (i.e., can be $Y_2$) include alcohol, aldehyde, epoxysuccinate, acid halide, carbonyl, halomethane, and diazomethane groups.

A peptide compound of the invention can comprise additional peptidic structures at the amino and/or carboxy terminus of the core nine amino acid structures (represented by (Xaa)$_a$ and (Xaa)$_b$ in the formula above). In one embodiment, a and b are, independently, integers from 1–15. In another embodiment, a and b are, independently, integers from 1–10. In yet another embodiment, a and b are, independently, integers from 1–5.

In another embodiment, the invention provides specific peptide compounds identified based on their ability to bind FGFR2-IIIC. Accordingly, the invention provides peptide compounds selected from the group consisting of SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; and SEQ ID NO: 44. Preferred peptide compounds include SEQ ID NO: 32, SEQ ID NO: 33, SEQ ID NO: 39, SEQ ID NO: 42, SEQ ID NO: 43 and SEQ ID NO: 44.

In yet another embodiment, the invention provides specific peptide compounds identified based on their ability to bind bFGF. Accordingly, the invention provides peptide compounds selected from the group consisting of SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; and SEQ ID NO: 68. Preferred peptide compounds include SEQ ID NO: 63 and SEQ ID NO: 68.

The peptide compounds of the invention can be prepared by standard peptide synthesis methods known in the art. Non-limiting examples of peptide syntheses are described further in Example 1. The ability of a peptide compound of the invention to bind to an FGF or FGFR can be evaluated using binding assays such as those described in Example 2. The ability of a peptide compound of the invention to modulate FGFR activity can be evaluated using an assay that measures FGFR activity, such as the functional assays described in Example 4.

II. Pharmaceutical Compositions

Another aspect of the invention pertains to pharmaceutical compositions of the peptide compounds of the invention. The pharmaceutical compositions of the invention typically comprise a peptide compound of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., a peptide compound of the invention) preferably is formulated in the composition in a therapeutically effective amount. A "therapeutically effective amount" refers to an amount effective, at dosages and for periods of time necessary, to achieve the desired therapeutic result, such as modulation of FGFR activity to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result, for example, modulation of FGFR activity for prophylactic purposes. Typically, since a prophylactic dose is used in subjects prior to or at an earlier stage of disease, the prophylactically effective amount will be less than the therapeutically effective amount.

The amount of active compound in the composition may vary according to factors isuch as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A peptide compound of the invention can be formulated into a pharmaceutical composition wherein the compound is the only active agent therein. Alternatively, the pharmaceutical composition can contain additional active agents. For example, two or more peptide compounds of the invention may be used in combination. Moreover, a peptide compound of the invention can be combined with one or more other agents that have modulatory effects on FGFR activity.

A pharmaceutical composition of the invention, comprising a peptide compound of the invention, can be administered to a subject to modulate FGFR activity in cells of the subject (discussed in further detail below in subsection III). As used herein, the term "subject" is intended to include living organisms in which an FGFR activity occurs, e.g., mammals. Examples of subjects include humans, dogs, cats, mice, rats, and transgenic species thereof.

III. Modulatory Methods

The peptide compounds of the invention can be used to modulate FGFR activity in a cell expressing the FGFR. A peptide compound of the invention may be an agonist or an antagonist of FGFR activity (which can be evaluated using a functional assay of FGFR activity, such as those described in Example 4). Accordingly, the various forms of the term "modulating" as used herein is intended to include "stimulating" FGFR activity and "inhibiting" FGFR activity.

In one embodiment, the invention provides a method of modulating fibroblast growth factor receptor (FGFR) activity in a cell comprising contacting a peptide compound of the invention with a cell expressing FGFR such that FGFR activity in the cell is modulated. In a preferred embodiment, the FGFR is FGFR2-IIIC. For peptide compounds of the invention that bind FGF, rather than FGFR (including SEQ ID NOs: 45–68), the method can comprise contacting the peptide compound with a cell expressing FGFR in the presence of an FGF such that FGFR activity in the cell is modulated. In a preferred embodiment, the FGF is basic FGF.

In one embodiment of the modulatory methods of the invention, the peptide compound is contacted with the cell expressing FGFR in vitro. For example, the peptide compound can be added to the culture medium in which the cells are cultured in vitro. In another embodiment of the modulatory methods of the invention, the peptide compound is administered to a subject such that the peptide compound is contacted with a cell expressing FGFR in vivo. Peptide compounds can be administered to a subject as described above in subsection II.

The modulatory methods of the invention may be useful in a variety of clinical situations that may involve enhanced or diminished FGFR activity. For example, agonists of FGFR activity may be useful in disease situations in which there is insufficient angiogenesis, such as ulcers, stroke, heart disease, infertility and scleroderma. Alternatively, antagonists of FGFR activity may be useful in disease situations in which there is excess or aberrant angiogenesis, such as rheumatoid arthritis, cancer, diabetic blindness, Kaposi's sarcoma and psoriasis. Other particular disease situations in which the modulatory methods of the invention may be useful include restinosis, wound healing, prostate cancer, pancreatic cancer and leukemia.

This invention is further illustrated by the following examples which should not be construed as limiting. The contents of all references, patents and published patent applications cited throughout this application are hereby incorporated by reference. The Sequence Listing described herein is intended to be part of the present specification.

EXAMPLE 1

Peptide Synthesis

Peptide compounds of the invention can be prepared by solid-phase peptide synthesis using an $N^\alpha$-9-fluorenylmethyloxycarbonyl (FMOC)-based protection strategy as follows. Starting with 2.5 mmoles of FMOC-Val-Wang resin, sequential additions of each amino acid are performed using a four-fold excess of protected amino acids, 1-hydroxybenzotriazole (HOBt) and diisopropyl carbodiimide (DIC). Recouplings are performed when necessary as determined by ninhydrin testing of the resin after coupling. Each synthesis cycle is minimally described by a three minute deprotection (25% piperidine/N-methyl-pyrrolidone (NMP)), a 15 minute deprotection, five one minute NMP washes, a 60 minute coupling cycle, five NMP washes and a ninhydrin test. The peptide is removed from the resin by treatment with trifluoroacetic acid (TFA) (82.5%), water (5%), thioanisole (5%), phenol (5%), ethanedithiol (2.5%) for two hours followed by precipitation of the peptide in cold ether. The solid is pelleted by centrifugation (2400 rpm×10 min.), and the ether decanted. The solid is resuspended in ether, pelleted and decanted a second time. The solid is dissolved in 10% acetic acid and lyophilized to dryness.

Alternatively, peptide compounds of the invention can be prepared on an Advanced ChemTech Model 396 multiple peptide synthesizer using an automated protocol established by the manufacturer for 0.025 mmole scale synthesis. Double couplings are performed on all cycles using 2-(1H-benzotriazol-1-yl)-1,1,3,3-tetramethyluronium hexafluorophosphate (HBTU)/N,N-diisopropylethylamine (DIEA)/HOBt/FMOC-AA in four-fold excess for 30 minutes followed by DIC/HOBt/FMOC-AA in four-fold excess for 45 minutes. The peptide is deprotected and removed from the resin by treatment with TFA/water (95%/5%) for three hours and precipitated with ether as described above. The pellet is resuspended in 10% acetic acid and lyophilized. The material is purified by a preparative HPLC using 15%–40% acetonitrile over 80 minutes on a Vydac C18 column (21× 250 mm).

EXAMPLE 2

FGF Receptor Binding Assays

The ability of a peptide compound to bind to an FGF receptor can be determined using one or both of the receptor binding assays described in this example, which measure the ability of a test compound to inhibit the binding of radiolabeled bFGF to the FGF receptor. The first assay is a cell-based assay, utilizing FGF receptor-expressing cells. Cells expressing an FGF receptor are seeded on a 96 well plate (50,000 cells/well) and incubated overnight at 37° C., 5% $CO_2$. The cells are then washed once with binding buffer (Dulbecco's Modified Eagle's Medium (DMEM) with HEPES, gelatin and heparin). A test peptide is diluted to the desired concentration in binding buffer with heparin (15 U/ml) and added to the cells (25 µl per well). $^{125}$I-bFGF (50,000 cpm/well; Amersham Life Sciences), diluted in binding buffer with heparin, is added to each well (25 µl per well so that final volume is 50 µl). The cells are incubated in a humidified chamber at 4° C. for 3 hours. The cells are washed twice with binding buffer to remove unbound material. The washed cells are then dissolved in 100 µl of 1N NaOH and counted in a gamma counter. The ability of a test compound to bind to FGFR is evidenced by the reduced binding of $^{125}$I-bFGF to the cells in the presence of the test compound as compared to the binding of $^{125}$I-bFGF to the cells in the absence of the test compound.

A second FGFR binding assay utilizes biotinylated soluble FGFR. Biotinylated FGFR is mixed in an eppendorf tube with $^{125}$I-bFGF and a test compound in binding buffer. The tubes are placed on an eppendorf roller at 4° C. for 1.5 hours. Magnetic streptavidin beads (CPG, Inc.) are prepared by washing twice with binding buffer. After the 1.5 hour incubation of the tubes, 15 µl of magnetic streptavidin beads are added to each tube and continued on the eppendorf roller for 10 minutes at 4° C. to allow the strepavidin to interact with the biotinylated FGFR. The tubes are removed from the roller and spun down in a microfuge for 2 minutes at 3000 rpm. Using magnets, the magnetic beads are washed twice with binding buffer. 100 µl of binding buffer is added to each tube and the contents are moved to a 12×75 mm test tube. The contents (i.e., strepavidin beads, with biotinylated FGFR and $^{125}$I-bFGF bound thereto) are counted in a Gamma counter. The ability of a test compound to bind to FGFR is evidenced by the reduced binding of $^{125}$I-bFGF to the biotinylated FGFR in the presence of the test compound as compared to the binding of $^{125}$I-bFGF to the biotinylated FGFR in the absence of the test compound.

EXAMPLE 3

FGF Binding Assay

A phage display library can be screened for compounds that bind to bFGF using a biopanning assay as described in this example. Basic FGF is bound to heparin agarose beads in 0.5 M NaCl/phosphate buffered saline (PBS) with 0.1% fish gelatin overnight at 4° C. Sufficient bFGF is added to saturate the heparin (approximately 3.5 mg/ml resin). The beads are washed at least three times with 0.5 M NaCl/PBS and then washed at least three times with 1×PBS. The phage display library ($10^{11}$ phage) is preincubated with 50 µl of heparin beads (not coated with bFGF) in 1×PBS/0.1% fish gelatin (v/v) for 1 hour at 4° C. and the phage are recovered by filtering through cellulose acetate 0.45 microfuge filters at 3000 rpm for 3 minutes. The recovered phage are incubated with 50 µl of coated beads (bFGF-heparin) at 4° C. for 2–4 hours. The beads are washed and resuspended with 200–1000 µl of 1×PBS/0.05% Tween at 4° C. The beads are spun down and the washing step is repeated 7–10 times as fast as reasonable. Bound phage are eluted from the beads at 20° C. with 2.5 M NaCl/PBS for 20–30 minutes. The beads are removed by filtration and the phage are recovered. The inserts of phage that bind bFGF are sequenced to identify peptide compounds capable of binding bFGF.

EXAMPLE 4

Functional Assays of FGF Receptor Activity

The effect of peptide compounds on the functional activity of an FGF receptor can be evaluated in one or both of the functional assays described in this example. The first assay is a signal transduction assay, exploiting the fact that bFGF binding to FGFR initiates a phosphorylation cascade that includes the phosphorylation of MAP kinase (MAP-K). Accordingly, the ability of a test compound to modulate bFGF-induced phosphorylation of MAP-K is examined. NIH 3T3 cells are synchronized to quiescence by growing in medium containing 0.5% fetal bovine serum (FBS) for 2 days. The cells are then shifted into fresh 0.5% FBS-containing medium for 2 hours to reduce the basal level of MAP-K phosphorylation before the experiment. Test peptide compounds are dissolved in fresh dimethyl sulfoxide (DMSO) to 100 mg/ml and series dilutions are made in DMSO. Peptides at various dilutions are added to medium containing bFGF (1 or 10 µM). Phosphorylation of MAP-K in the 3T3 cells is initiated by incubating the cells with the bFGF-containing medium in the presence or absence of test peptide for 15 minutes at 37° C. The phosphorylation is stopped by washing with cells with PBS and lysing the cells with sodium dodecyl sulfide (SDS)-containing buffer. Cell lysates are separated on 12% SDS polyacrylamide gels and the proteins are transferred onto PVDF membranes. Membrane-bound cellular proteins are probed with a rabbit anti-phosphoMAP-K antibodies, followed by a goat anti-rabbit secondary antibody, labeled with horse radish peroxidase. The blots are then detected by the enhanced chemiluminescence (ECL) method.

A second functional assay for FGFR is a proliferation assay, based on the fact that NIH 3T3 cells show enhanced growth in the presence of increasing concentrations of bFGF. NIH 3T3 cells are cultured (e.g., about 3 days) with bFGF (10 nM) in the presence or absence of a test peptide compound. Cell growth is quantitated using a standard method for detecting cell growth, such as tritiated thymidine incorporation or uptake of 3, (4,4-dimethylthiazol-2-yl)2,5-diphenyl-tetrazolium bromide (MTT). MTT (commercially available from Sigma Chemical Co.) is a chromogenic substrate that is converted from yellow to blue in viable cells, which can be detected spectrophotometrically.

EXAMPLE 5

Peptide Compounds That Bind FGFR2-IIIC

A series of peptides capable of binding FGFR2-IIIC were identified and their amino acid sequences were aligned, as shown in Table 1:

TABLE 1

| | | | | | | | | | | | | | |
|---|---|---|---|---|---|---|---|---|---|---|---|---|---|
| | | D | V | F | L | D | M | Y | Q | F | S | V | I | SEQ ID NO: 2 |
| | | | | F | L | G | K | Y | M | E | S | L | M | R | M | SEQ ID NO: 3 |
| | | | | F | L | M | M | Y | M | M | | | | SEQ ID NO: 4 |
| | | | | Y | L | Y | L | Y | M | V | | | | SEQ ID NO: 5 |
| | | | | F | M | R | Q | Y | L | D | T | W | W | L | I | SEQ ID NO: 6 |
| | | E | V | F | Y | R | I | Y | L | S | V | L | L | SEQ ID NO: 7 |
| | | A | H | N | L | R | Q | Y | L | M | R | F | L | SEQ ID NO: 8 |
| T | A | G | D | P | L | T | Q | Y | R | M | R | | | SEQ ID NO: 9 |
| I | G | S | G | T | L | E | Q | Y | M | G | R | | | SEQ ID NO: 10 |
| | | | | Y | F | D | Q | Y | M | L | F | F | Y | D | SEQ ID NO: 11 |

TABLE 1-continued

| Sequence | SEQ ID NO |
|---|---|
| Y F G Q Y M A L Y | SEQ ID NO: 12 |
| S I Y F R E Y L L R A G | SEQ ID NO: 13 |
| Y V S L Y M N Y L G L L | SEQ ID NO: 14 |
| V F L S L Y Y D R M R Y | SEQ ID NO: 15 |
| G S Y L A L Y T E G L R | SEQ ID NO: 16 |
| F R Y L L Y Y M E S N R | SEQ ID NO: 17 |
| K A L E W Y K S L M R M | SEQ ID NO: 18 |
| Y L Y R Y A Q F R T S D | SEQ ID NO: 19 |
| Y S L T Y Q Y L L T V L | SEQ ID NO: 20 |
| R K Y F S L Y R N L L G | SEQ ID NO: 21 |
| G Y I E K Y K L A I G R | SEQ ID NO: 22 |
| X Y L S Y Y R S L T I S | SEQ ID NO: 23 |
| P L H L R I Y S N W L V | SEQ ID NO: 24 |
| Y L I L Y K Y | SEQ ID NO: 25 |
| L F I R Y Y K | SEQ ID NO: 26 |

The frequency of each observed amino acid at each position in the alignment were calculated, the results of which are summarized in Table 2:

TABLE 2

| | | | | | | | | | | | | | | | | | | |
|---|---|---|---|---|---|---|---|---|---|---|---|---|---|---|---|---|---|---|
| nonpolar | P | 0 | 0 | 1 | 0 | 1 | 0 | 0 | 0 | 0 | 0 | 0 | 0 | 0 | 0 | 0 | 0 | P |
| | C | 0 | 0 | 0 | 0 | 0 | 0 | 0 | 0 | 0 | 0 | 0 | 0 | 0 | 0 | 0 | 0 | C |
| | M | 0 | 0 | 0 | 0 | 0 | 1 | 1 | 2 | 0 | 3 | 0 | 2 | 1 | 1 | 1 | M |
| | G | 0 | 1 | 2 | 2 | 0 | 0 | 2 | 0 | 0 | 0 | 1 | 1 | 0 | 4 | 0 | 0 | G |
| aliphatic | A | 0 | 1 | 1 | 0 | 1 | 0 | 1 | 0 | 0 | 1 | 1 | 1 | 1 | 0 | 0 | 0 | A |
| | V | 0 | 0 | 0 | 3 | 0 | 1 | 0 | 0 | 0 | 0 | 1 | 1 | 3 | 1 | 0 | 0 | V |
| | L | 0 | 0 | 0 | 2 | 1 | 5 | 1 | 0 | 5 | 4 | 3 | 2 | 1 | L |
| | I | 1 | 0 | 0 | 1 | 0 | 2 | 1 | 2 | 0 | 0 | 0 | 1 | 2 | 0 | 1 | I |
| aromatic | W | 0 | 0 | 0 | 0 | 0 | 0 | 0 | 1 | 0 | 0 | 0 | 1 | 1 | 1 | 0 | 0 | W |
| | F | 0 | 0 | 1 | 0 | 5 | 0 | 0 | 0 | 0 | 1 | 2 | 2 | 0 | 0 | 0 | F |
| | Y | 0 | 0 | 1 | 0 | 5 | 1 | 3 | 3 | 5 | 1 | 1 | 1 | 1 | 1 | 0 | Y |
| | H | 0 | 0 | 0 | 1 | 1 | 0 | 0 | 0 | 0 | 0 | 0 | 0 | 0 | 0 | 0 | H |

TABLE 2-continued

| | | | | | | | | | | | | | | | | | | |
|---|---|---|---|---|---|---|---|---|---|---|---|---|---|---|---|---|---|---|
| positive | K | 0 | 0 | 0 | 2 | 0 | 0 | 0 | 2 | 0 | 4 | 0 | 0 | 0 | 0 | 0 | 0 | K |
| | R | 0 | 0 | 1 | 1 | 0 | 0 | 3 | 1 | 0 | 3 | 0 | 1 | 4 | 2 | 0 | R |
| negative | D | 0 | 0 | 1 | 1 | 0 | 0 | 2 | 0 | 0 | 0 | 2 | 0 | 0 | 0 | 1 | 1 | D |
| | E | 0 | 0 | 1 | 0 | 0 | 0 | 3 | 1 | 0 | 0 | 3 | 0 | 0 | 0 | 0 | 0 | E |
| polar | S | 0 | 0 | 2 | 2 | 0 | 0 | 4 | 0 | 0 | 1 | 3 | 3 | 0 | 0 | 2 | 0 | S |
| | T | 1 | 0 | 0 | 0 | 0 | 1 | 1 | 1 | 0 | 0 | 1 | 0 | 2 | 1 | 1 | 0 | 0 | T |
| | N | 0 | 0 | 0 | 0 | 1 | 0 | 0 | 0 | 0 | 0 | 3 | 0 | 1 | 0 | 0 | 0 | N |
| | Q | 0 | 0 | 0 | 0 | 0 | 0 | 0 | 0 | 2 | 0 | 1 | 1 | 0 | 0 | 0 | 0 | Q |
| SUM | | 2 | 2 | 11 | 15 | 25 | 25 | 25 | 25 | 25 | 25 | 24 | 21 | 19 | 18 | 9 | 4 | |

The strongest consensus resides over nine amino acids. The most common amino acids at each of these nine positions are: (Y/F)-(L/F/I)-(R/D/E/S/Y/G)-(Q/L/Y)-Y-(M/L/K/R)-(L/M/D/E/N/S)-(R/L/S/T)-(L/F/M/V) (SEQ ID NO: 1). More preferred amino acids at each position are shaded in dark gray in Table 2, less preferred amino acids are shaded in light gray.

Select peptides were synthesized (e.g., as described in Example 1) and tested in binding, proliferation and signal transduction assays (as described in Examples 2 and 4). The results of these assays are summarized in Table 3:

TABLE 3

| Ref. # | Sequence | SEQ ID NO: | Binding IC$_{50}$ | Proliferation IC$_{50}$ | MAP-K |
|---|---|---|---|---|---|
| 564 | H-GYYLLWMVG-OH*TFA | 27 | >100 µM | ND | ND |
| 656 | H-GYLYLYMVG-OH*TFA | 28 | >100 µM | ND | ND |
| 566 | H-GFLMMYMMG-OH*TFA | 29 | >100 µM | ND | ND |
| 567 | H-GYFQYMALYG-OH*TFA | 30 | >100 µM | ND | ND |
| 622 | H-GDVFLSMYQFSVIG-OH*TFA | 31 | >100 µM | ND | ND |
| 623 | H-GAHNLRQYLMRFLG-OH*TFA | 32 | ~120 µM | ~100 µM | ~50 µM |
| 658 | H-GAHYLRQYLMRFLG-NH*TFA | 33 | ~8 µM | ND | ~1 µM |
| 659 | H-GFLGKYMESLMRMG-NH*TFA | 34 | ~300 µM | ND | ND |
| 660 | Acetyl-GHDGEMYG-OH | 35 | >1 mM | ND | ND |
| 661 | H-GKALEWYKSLMRMG-NH*TFA | 36 | ~300 µM | ND | ND |
| 662 | H-GYLAQYMARG-NH*TFA | 37 | ~300 µM | ND | ND |
| 663 | H-GSLMRMG-NH*TFA | 38 | >1 mM | ND | ND |
| 668 | H-GAHYLRQYLMRFRG-NH*TFA | 39 | ~3 µM | ND | ND |
| 669 | H-GAHYLRQYMMRFLG-NH*TFA | 40 | ~20 µM | ND | ND |
| 670 | H-LRQYLMRFR-NH*TFA | 41 | ~120 µM | ND | ND |
| 671 | H-YLRQYLMRFR-NH*TFA | 42 | ~8 µM | ND | ND |
| 672 | H-HYLRQYLMRFR-NH*TFA | 43 | ~8 µM | ND | ND |
| 673 | H-AYLRQYLMRFR-NH*TFA | 44 | ~8 µM | ND | ND |

As shown in Table 3, compound 623 inhibits the binding of bFGF to FGFR2-IIIC with an IC$_{50}$ of about 120 µM. Additional increases in the binding ability of the peptide were achieved by synthesizing amino-acid substituted derivatives of compound 623 that more closely approximate the amino acids of the consensus sequence of SEQ ID NO: 1. These derivatives include compound 658 (containing an N4Y change) and compound 668 (containing N4Y and L13R changes), which have IC$_{50}$s of about 8 and 3 µM, respectively. The effect of compounds 623 and 658 on $^{125}$I-bFGF binding to soluble biotinylated FGF receptor (in comparison to unlabeled bFGF) is shown in the graph of FIG. 1.

Figure 2:
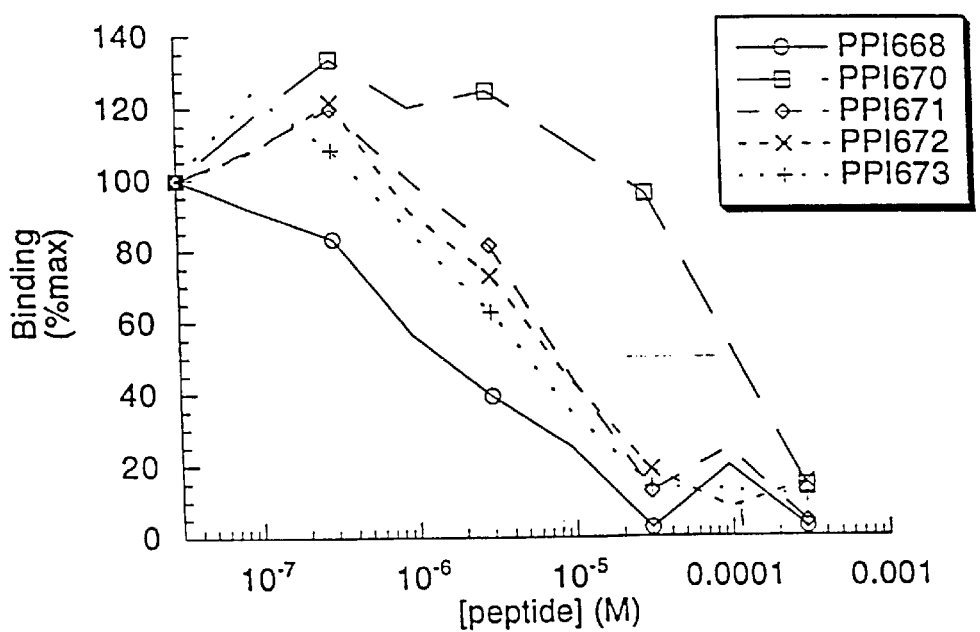
FIG. 2 is a graph depicting the inhibitory effect of compounds 668, 670, 671, 672 and 673 on bFGF binding to FGF receptor.

A deletion series of compound 668 was prepared (compounds 670, 671, 672 and 673). As shown in Table 3, removal of both terminal glycines (compound 673) increases the IC$_{50}$ from about 3 µM to about 8 µM, while additional deletion of the amino terminal histidine (compound 671) does not appear to further increase the IC$_{50}$. However, deletion of the tyrosine (compound 670) greatly increases the IC$_{50}$ to about 120 µM, consistent with tyrosine being highly conserved at this position in the selected peptides. The inhibitory effect of compounds 668, 670, 671, 672 and 673 on FGF binding is illustrated in the graph of FIG. 2.

Figure 3:
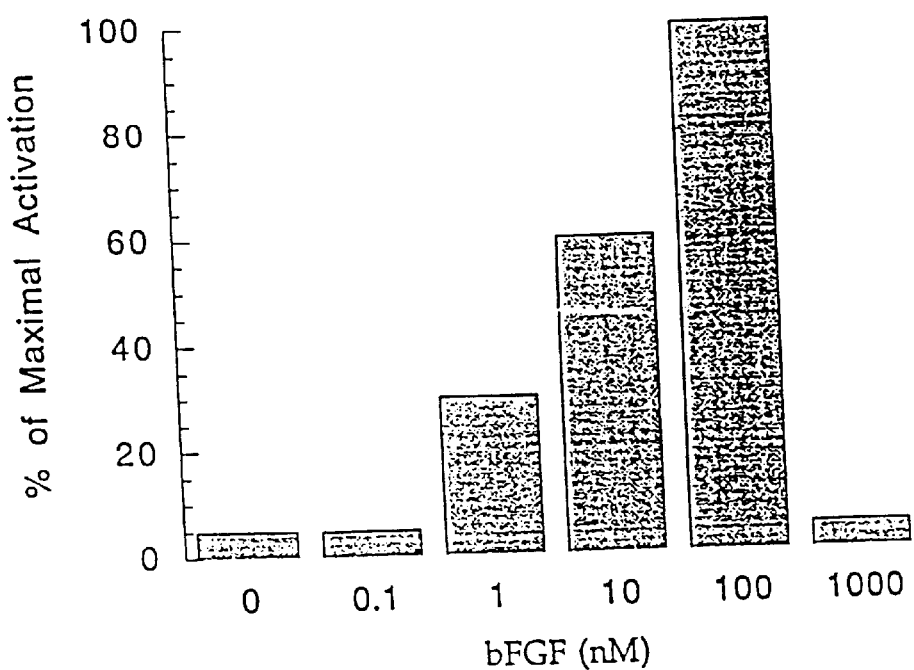
FIG. 3 is a bar graph depicting the activation of p42-MAP kinase by bFGF in NIH 3T3 cells.
Figure 4:
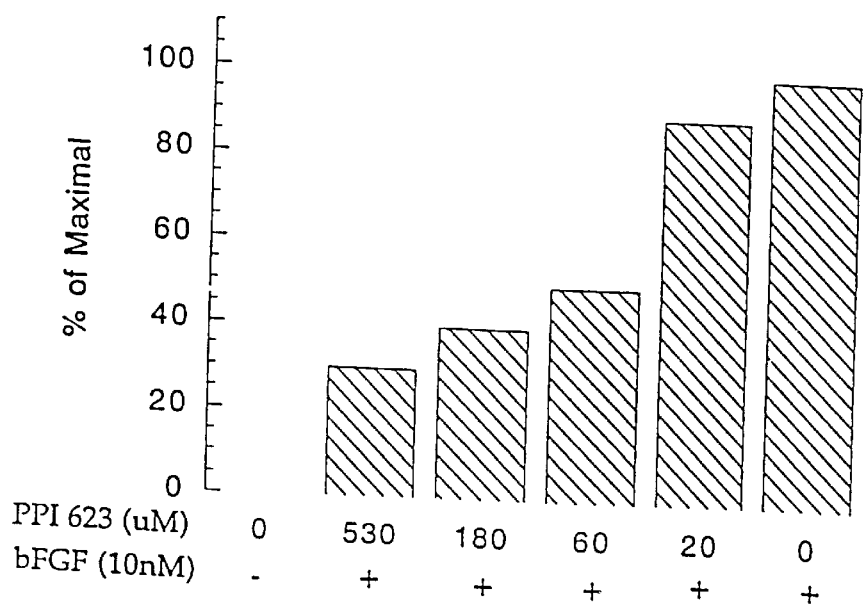
FIG. 4 is a bar graph depicting the antagonizing effect of compound 623 on the activation of p42-MAP kinase by bFGF in NIH 3T3 cells.
Figure 5:
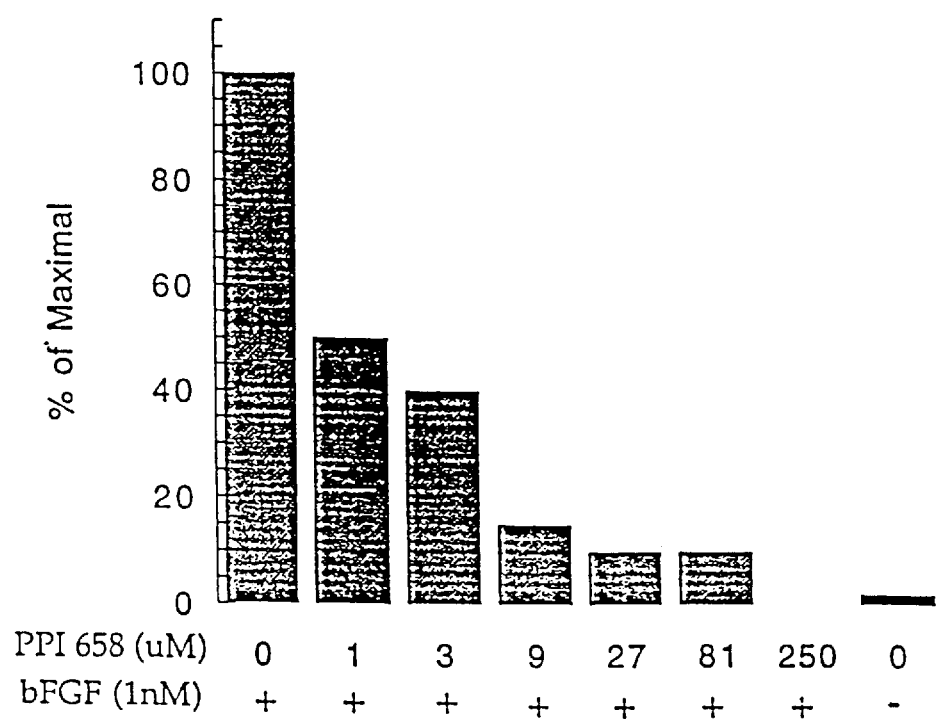
FIG. 5 is a bar graph depicting the antagonizing effect of compound 658 on the activation of p42-MAP kinase by bFGF in NIH 3T3 cells.

To determine whether particular compounds were agonists or antagonist of bFGF binding to FGFR, the functional effect of these peptides on FGFR were assayed using the MAP kinase and 3T3 cell proliferation assays described in Example 4. Control experiments (without test peptide compounds) determined that concentrations of 1 and 10 nM induce 40–60% activation of MAP-K (illustrated in the graph of FIG. 3). However, in the presence of increasing concentrations of compound 623 (which has an IC$_{50}$ of about 120 µM in the binding assay), the activation of MAP-K is clearly antagonized (illustrated in the graph of FIG. 4). The 50% reduction in activation occurs between 180 and 60 µM of compound 623. Compound 658 (which has a lower IC$_{50}$ of about 8 µM) half maximally antagonizes 1 nM bFGF at about 3 µM (illustrated in the graph of FIG. 5).

Figure 6:
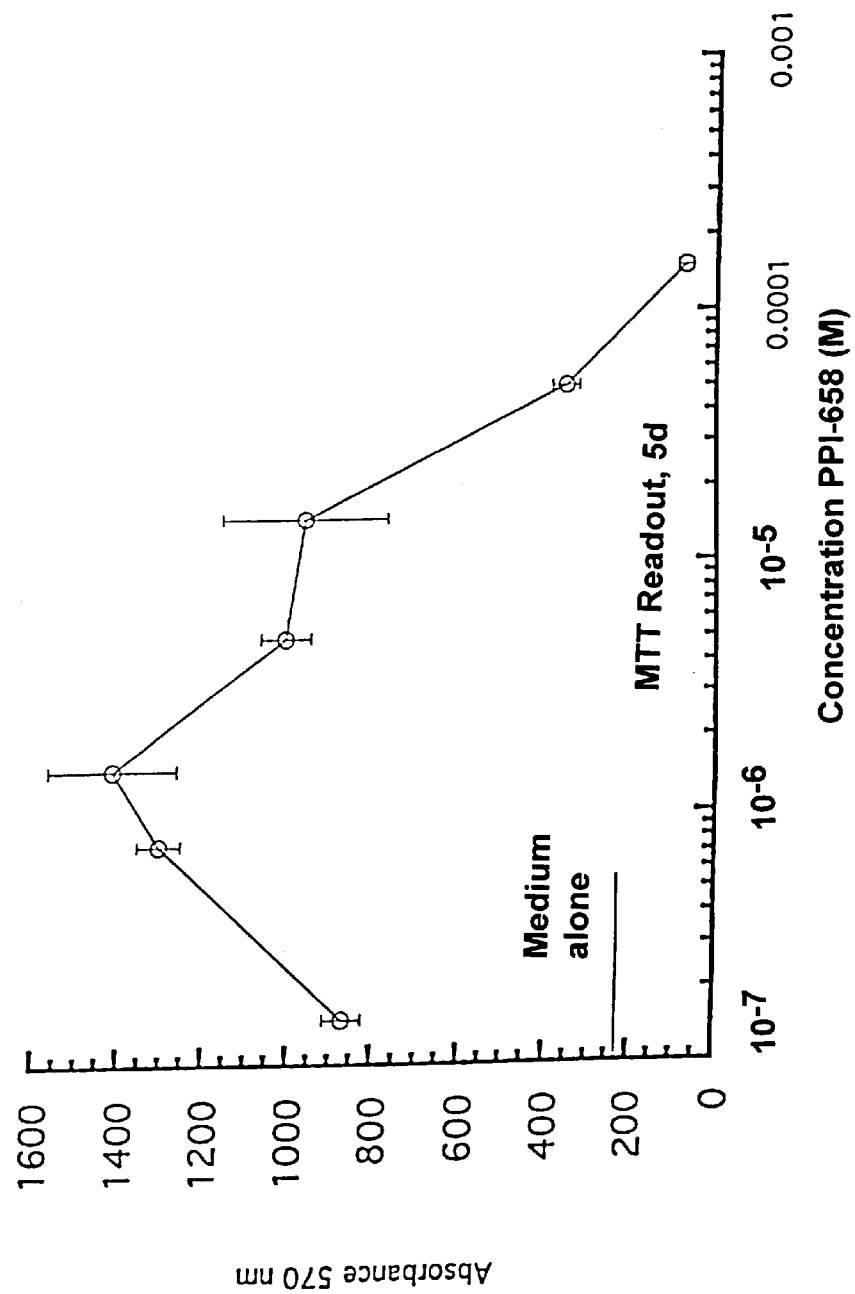
FIG. 6 is a graph depicting the inhibition of bFGF-induced proliferation of NIH 3T3 cells in the presence of compound 658 and 10 nM bFGF.

In the NIH 3T3 cell proliferation assay, proliferation of the cells induced by the presence of 10 nM bFGF is reduced by compound 658 half maximally at 40 µM (illustrated in the graph of FIG. 6).

EXAMPLE 6

Peptide Compounds That Bind bFGF

Basis FGF was panned with a phage display library as described in Example 3. Selected peptides capable of binding to bFGF are summarized in Table 4:

TABLE 4

| | |
|---|---|
| R G R G I G F | SEQ ID NO: 45 |
| S L R G F G R | SEQ ID NO: 46 |
| Y D W D D L L G | SEQ ID NO: 47 |
| Y T W D Y L L G | SEQ ID NO: 48 |
| Y D W D S I L G | SEQ ID NO: 49 |
| Y D W D D L L S | SEQ ID NO: 50 |
| I D W D D L L S | SEQ ID NO: 51 |
| S W G D W E R S G D W F | SEQ ID NO: 52 |
| W G G W E W T G L W S Y | SEQ ID NO: 53 |
| C V L L Y D V W T C | SEQ ID NO: 54 |
| C V L L Y D E R T C | SEQ ID NO: 55 |
| C F D L Y H Y V Y C | SEQ ID NO: 56 |
| C V D L Y H L Y C | SEQ ID NO: 57 |
| C V D L Y H Y V Y C | SEQ ID NO: 58 |

Select peptides were synthesized (e.g., as described in Example 1) and tested in binding, proliferation and signal transduction assays (as described in Examples 2 and 4). The results of these assays are summarized in Table 5:

TABLE 5

| Ref. # | Sequence | SEQ ID NO: | Binding IC$_{50}$ | Proliferation IC$_{50}$ | MAP-K |
|---|---|---|---|---|---|
| 475 | H-ADGAAGYDWDDLLSGAA-NH*TFA | 59 | >100 µM | >100 µM | ND |
| 476 | Biotin-ADGAAGYDWDDLLSGAA-NH | 60 | >100 µM | >100 µM | ND |
| 477 | H-ADGAAGYDWDDLLGGAA-NH*TFA | 61 | >100 µM | >100 µM | ND |
| 478 | Biotin-ADGAAGYDWDDLLGGAA-NH | 62 | >100 µM | >100 µM | ND |
| 507 | H-ADGAAGCVDLYHYVYCGGAA-NH*TFA | 63 | >100 µM | 10–100 µM | ND |
| 508 | H-ADGAAGCVLLYDVWTCGGAA-NH*TFA | 64 | ND | >1 mM | ND |
| 509 | H-ADGAAGSWGDWERSGDWFGGAA-NH*TFA | 65 | >100 µM | >100 µM | ND |
| 512 | Acetyl-GSWGDWERSGDWFG-NH | 66 | >100 µM | >100 µM | ND |
| 513 | Acetyl-GCVLLYDERTCG-NH | 67 | >100 µM | >100 µM | ND |
| 514 | Acetyl-GCVDLYHYVYCG-NH | 68 | >100 µM | 10–100 µM | ~50 µM |

The results shown in Table 5 demonstrate that compounds 507 and 514 (which comprise the same core amino acid sequence) are antagonists of the proliferative activity of bFGF.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A peptide compound comprising an amino acid sequence:

$$Y_1\text{-Xaa1-Xaa2-Xaa3-Xaa4-Xaa5-Xaa6-Xaa7-Xaa8-Xaa9-}Y_2 \quad \text{(SEQ ID NO: 1)}$$

wherein:

$Y_1$ is hydrogen, an amino-derivative group or a peptidic structure having a formula $(Xaa)_a$ wherein Xaa is any amino acid structure and a is an integer from 1–15 inclusive;

$Y_2$ is hydrogen, a carboxy-derivative group or a peptidic structure having a formula $(Xaa)_b$ wherein Xaa is any amino acid structure and b is an integer from 1–15 inclusive;

Xaa1 is a tyrosine residue, a phenylalanine residue, a pyridylalanine residue, or a homophenylalanine residue;

Xaa2 is a leucine residue, a norleucine residue, a phenylalanine residue, a pyridylalanine residue, a homophenylalanine residue, or an isoleucine residue;

Xaa3 is an arginine residue, an aspartic acid residue, a glutamic acid residue, a serine residue, a tyrosine residue, or a glutamine residue;

Xaa4 is a glutamine residue, a leucine residue, a norleucine residue, or a tyrosine residue;

Xaa5 is a tyrosine residue;

Xaa6 is a methionine residue, a leucine residue, a norleucine residue, a lysine residue, or an arginine residue;

Xaa7 is a leucine residue, a norleucine residue, a methionine residue, an aspartic acid residue, a glutamic acid residue, an asparagine residue, or a serine residue;

Xaa8 is an arginine residue, a leucine residue, a norleucine residue, a serine residue, or a threonine residue; and Xaa9 is a leucine residue, a norleucine residue, a phenylalanine residue, a pyridylalanine residue, a homophenylalanine residue, a methionine residue, or a valine residue;

or an inverso or retro-inverso isomer thereof.

2. A peptide compound selected from the group consisting of SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; and SEQ ID NO: 44.

3. The peptide compound of claim 2, which is SEQ ID NO: 32.

4. The peptide compound of claim 2, which is SEQ ID NO: 33.

5. The peptide compound of claim 2, which is SEQ ID NO: 39.

6. The peptide compound of claim 2, which is SEQ ID NO: 42.

7. The peptide compound of claim 2, which is SEQ ID NO: 43.

8. The peptide compound of claim 2, which is SEQ ID NO: 44.

9. A peptide compound selected from the group consisting of SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; and SEQ ID NO: 68.

10. The peptide compound of claim 9, which is SEQ ID NO: 63.

11. The peptide compound of claim 9, which is SEQ ID NO: 68.

12. A pharmaceutical composition comprising a peptide compound of claim 1 and a pharmaceutically acceptable carrier.

13. A pharmaceutical composition comprising a peptide compound of claim 2 and a pharmaceutically acceptable carrier.

14. A pharmaceutical composition comprising a peptide compound of claim 9 and a pharmaceutically acceptable carrier.

* * * * *

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /note= Xaa is Tyr or Phe (ix) FEATURE:
        (A) NAME/KEY: Modified-site
        (B) LOCATION: 2
        (D) OTHER INFORMATION: /note= Xaa is Leu, Phe or Ile (ix) FEATURE:
        (A) NAME/KEY: Modified-site
        (B) LOCATION: 3
        (D) OTHER INFORMATION: /note= Xaa is Arg, Asp, Glu, Ser, Tyr
            or Gly (ix) FEATURE:
        (A) NAME/KEY: Modified-site
        (B) LOCATION: 4
        (D) OTHER INFORMATION: /note= Xaa is Gln, Leu or Tyr (ix) FEATURE:
        (A) NAME/KEY: Modified-site
        (B) LOCATION: 6
        (D) OTHER INFORMATION: /note= Xaa is Met, Leu, Lys or Arg (ix) FEATURE:
        (A) NAME/KEY: Modified-site
        (B) LOCATION: 7
        (D) OTHER INFORMATION: /note= Xaa is Leu, Met, Asp, Glu, Asn
            or Ser (ix) FEATURE:
        (A) NAME/KEY: Modified-site
        (B) LOCATION: 8
        (D) OTHER INFORMATION: /note= Xaa is Arg, Leu, Ser or Thr (ix) FEATURE:
        (A) NAME/KEY: Modified-site
        (B) LOCATION: 9
        (D) OTHER INFORMATION: /note= Xaa is Leu, Phe, Met or Val (xi) SEQUENCE DESCRIPTION: SEQ ID NO:1:

Xaa Xaa Xaa Xaa Tyr Xaa Xaa Xaa Xaa
1               5

(2) INFORMATION FOR SEQ ID NO:2:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:2:

```
Asp Val Phe Leu Asp Met Tyr Gln Phe Ser Val Ile
1               5                   10
```

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Phe Leu Gly Lys Tyr Met Glu Ser Leu Met Arg Met
1               5                   10
```

(2) INFORMATION FOR SEQ ID NO:4:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Phe Leu Met Met Tyr Met Met
1               5
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Tyr Leu Tyr Leu Tyr Met Val
1               5
```

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Phe Met Arg Gln Tyr Leu Asp Thr Trp Trp Leu Ile
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

Glu Val Phe Tyr Arg Ile Tyr Leu Ser Val Leu Leu
1               5                   10

(2) INFORMATION FOR SEQ ID NO:8:

(i) SEQUENCE CHARACTERISTICS:
             (A) LENGTH: 12 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:8:

Ala His Asn Leu Arg Gln Tyr Leu Met Arg Phe Leu
1               5                   10

(2) INFORMATION FOR SEQ ID NO:9:

(i) SEQUENCE CHARACTERISTICS:
             (A) LENGTH: 12 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:9:

Thr Ala Gly Asp Pro Leu Thr Gln Tyr Arg Met Arg
1               5                   10

(2) INFORMATION FOR SEQ ID NO:10:

(i) SEQUENCE CHARACTERISTICS:
             (A) LENGTH: 12 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:10:

Ile Gly Ser Gly Thr Leu Glu Gln Tyr Met Gly Arg
1               5                   10

(2) INFORMATION FOR SEQ ID NO:11:

(i) SEQUENCE CHARACTERISTICS:
             (A) LENGTH: 11 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:11:

Tyr Phe Asp Gln Tyr Met Leu Phe Phe Tyr Asp
1               5                   10

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

Tyr Phe Gly Gln Tyr Met Ala Leu Tyr
1               5

(2) INFORMATION FOR SEQ ID NO:13:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

Ser Ile Tyr Phe Arg Glu Tyr Leu Leu Arg Ala Gly
1               5                   10

(2) INFORMATION FOR SEQ ID NO:14:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

Tyr Val Ser Leu Tyr Met Asn Tyr Leu Gly Leu Leu
1               5                   10

(2) INFORMATION FOR SEQ ID NO:15:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

Val Phe Leu Ser Leu Tyr Tyr Asp Arg Met Arg Tyr
1               5                   10

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

Gly Ser Tyr Leu Ala Leu Tyr Thr Glu Gly Leu Arg
1               5                   10

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

Phe Arg Tyr Leu Leu Tyr Tyr Met Glu Ser Asn Arg
1               5                   10

(2) INFORMATION FOR SEQ ID NO:18:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

Lys Ala Leu Glu Trp Tyr Lys Ser Leu Met Arg Met
1               5                   10

(2) INFORMATION FOR SEQ ID NO:19:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

Tyr Leu Tyr Arg Tyr Ala Gln Phe Arg Thr Ser Asp
1               5                   10

(2) INFORMATION FOR SEQ ID NO:20:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

Tyr Ser Leu Thr Tyr Gln Tyr Leu Leu Thr Val Leu
1               5                   10

(2) INFORMATION FOR SEQ ID NO:21:

(i) SEQUENCE CHARACTERISTICS:
        (A) LENGTH: 12 amino acids
        (B) TYPE: amino acid (D) TOPOLOGY: linear (ii) MOLECULE TYPE: peptide (v) FRAGMENT TYPE: internal (xi) SEQUENCE DESCRIPTION: SEQ ID NO:21:

Arg Lys Tyr Phe Ser Leu Tyr Arg Asn Leu Leu Gly
1               5                   10

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

Gly Tyr Ile Glu Lys Tyr Lys Leu Ala Ile Gly Arg
1               5                   10

(2) INFORMATION FOR SEQ ID NO:23:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Xaa Tyr Leu Ser Tyr Tyr Arg Ser Leu Thr Ile Ser
1               5                   10

(2) INFORMATION FOR SEQ ID NO:24:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Pro Leu His Leu Arg Ile Tyr Ser Asn Trp Leu Val
1               5                   10

(2) INFORMATION FOR SEQ ID NO:25:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

Tyr Leu Ile Leu Tyr Lys Tyr
1               5

(2) INFORMATION FOR SEQ ID NO:26:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

```
Leu Phe Ile Arg Tyr Tyr Lys
1               5
```

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

```
Gly Tyr Tyr Leu Leu Trp Met Val Gly
1               5
```

(2) INFORMATION FOR SEQ ID NO:28:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:28:

```
Gly Tyr Leu Tyr Leu Tyr Met Val Gly
1               5
```

(2) INFORMATION FOR SEQ ID NO:29:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

```
Gly Phe Leu Met Met Tyr Met Met Gly
1               5
```

(2) INFORMATION FOR SEQ ID NO:30:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Gly Tyr Phe Gln Tyr Met Ala Leu Tyr Gly
1               5                   10

(2) INFORMATION FOR SEQ ID NO:31:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

Gly Asp Val Phe Leu Ser Met Tyr Gln Phe Ser Val Ile Gly
1               5                   10

(2) INFORMATION FOR SEQ ID NO:32:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

Gly Ala His Asn Leu Arg Gln Tyr Leu Met Arg Phe Leu Gly
1               5                   10

(2) INFORMATION FOR SEQ ID NO:33:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

Gly Ala His Tyr Leu Arg Gln Tyr Leu Met Arg Phe Leu Gly
1               5                   10

(2) INFORMATION FOR SEQ ID NO:34:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

Gly Phe Leu Gly Lys Tyr Met Glu Ser Leu Met Arg Met Gly
1               5                   10

(2) INFORMATION FOR SEQ ID NO:35:

(i) SEQUENCE CHARACTERISTICS:
        (A) LENGTH: 8 amino acids (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

Gly His Asp Gly Glu Met Tyr Gly
1               5

(2) INFORMATION FOR SEQ ID NO:36:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

Gly Lys Ala Leu Glu Trp Tyr Lys Ser Leu Met Arg Met Gly
1               5                   10

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:37:

Gly Tyr Leu Ala Gln Tyr Met Ala Arg Gly
1               5                   10

(2) INFORMATION FOR SEQ ID NO:38:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:38:

Gly Ser Leu Met Arg Met Gly
1               5

(2) INFORMATION FOR SEQ ID NO:39:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

Gly Ala His Tyr Leu Arg Gln Tyr Leu Met Arg Phe Arg Gly
1               5                   10

(2) INFORMATION FOR SEQ ID NO:40:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:40:

```
Gly Ala His Tyr Leu Arg Gln Tyr Met Met Arg Phe Leu Gly
1               5                   10
```

(2) INFORMATION FOR SEQ ID NO:41:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:41:

```
Leu Arg Gln Tyr Leu Met Arg Phe Arg
1               5
```

(2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:42:

```
Tyr Leu Arg Gln Tyr Leu Met Arg Phe Arg
1               5                   10
```

(2) INFORMATION FOR SEQ ID NO:43:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:43:

```
His Tyr Leu Arg Gln Tyr Leu Met Arg Phe Arg
1               5                   10
```

(2) INFORMATION FOR SEQ ID NO:44:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:44:

Ala His Tyr Leu Arg Gln Tyr Leu Met Arg Phe Arg
1               5                  10

(2) INFORMATION FOR SEQ ID NO:45:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:45:

Arg Gly Arg Gly Ile Gly Phe
1               5

(2) INFORMATION FOR SEQ ID NO:46:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:46:

Ser Leu Arg Gly Phe Gly Arg
1               5

(2) INFORMATION FOR SEQ ID NO:47:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:47:

Tyr Asp Trp Asp Asp Leu Leu Gly
1               5

(2) INFORMATION FOR SEQ ID NO:48:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:48:

Tyr Thr Trp Asp Tyr Leu Leu Gly
1               5

(2) INFORMATION FOR SEQ ID NO:49:

(i) SEQUENCE CHARACTERISTICS:

(A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

Tyr Asp Trp Asp Ser Ile Leu Gly
1               5

(2) INFORMATION FOR SEQ ID NO:50:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

Tyr Asp Trp Asp Asp Leu Leu Ser
1               5

(2) INFORMATION FOR SEQ ID NO:51:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

Ile Asp Trp Asp Asp Leu Leu Ser
1               5

(2) INFORMATION FOR SEQ ID NO:52:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

Ser Trp Gly Asp Trp Glu Arg Ser Gly Asp Trp Phe
1               5                   10

(2) INFORMATION FOR SEQ ID NO:53:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:53:

Trp Gly Gly Trp Glu Trp Thr Gly Leu Trp Ser Tyr (2) INFORMATION FOR SEQ ID NO:54:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:54:

Cys Val Leu Leu Tyr Asp Val Trp Thr Cys
1               5                   10

(2) INFORMATION FOR SEQ ID NO:55:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:55:

Cys Val Leu Leu Tyr Asp Glu Arg Thr Cys
1               5                   10

(2) INFORMATION FOR SEQ ID NO:56:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:56:

Cys Phe Asp Leu Tyr His Tyr Val Tyr Cys
1               5                   10

(2) INFORMATION FOR SEQ ID NO:57:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:57:

Cys Val Asp Leu Tyr His Leu Tyr Cys
1               5

(2) INFORMATION FOR SEQ ID NO:58:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:58:

```
Cys Val Asp Leu Tyr His Tyr Val Tyr Cys
1               5                   10
```

(2) INFORMATION FOR SEQ ID NO:59:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:59:

```
Ala Asp Gly Ala Ala Gly Tyr Asp Trp Asp Asp Leu Leu Ser Gly Ala
1               5                   10                  15
Ala
```

(2) INFORMATION FOR SEQ ID NO:60:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:60:

```
Ala Asp Gly Ala Ala Gly Tyr Asp Trp Asp Asp Leu Leu Ser Gly Ala
1               5                   10                  15
Ala
```

(2) INFORMATION FOR SEQ ID NO:61:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:61:

```
Ala Asp Gly Ala Ala Gly Tyr Asp Trp Asp Asp Leu Leu Gly Gly Ala
1               5                   10                  15
Ala
```

(2) INFORMATION FOR SEQ ID NO:62:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:62:

Ala Asp Gly Ala Ala Gly Tyr Asp Trp Asp Asp Leu Leu Gly Gly Ala
1               5                   10                  15

Ala (2) INFORMATION FOR SEQ ID NO:63:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:63:

Ala Asp Gly Ala Ala Gly Cys Val Asp Leu Tyr His Tyr Val Tyr Cys
1               5                   10                  15

Gly Gly Ala Ala
        20

(2) INFORMATION FOR SEQ ID NO:64:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:64:

Ala Asp Gly Ala Ala Gly Cys Val Leu Leu Tyr Asp Val Trp Thr Cys
1               5                   10                  15

Gly Gly Ala Ala
        20

(2) INFORMATION FOR SEQ ID NO:65:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:65:

Ala Asp Gly Ala Ala Gly Ser Trp Gly Asp Trp Glu Arg Ser Gly Asp
1               5                   10                  15

Trp Phe Gly Gly Ala Ala
        20

(2) INFORMATION FOR SEQ ID NO:66:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:66:

```
Gly Ser Trp Gly Asp Trp Glu Arg Ser Gly Asp Trp Phe Gly
1               5                   10
```

(2) INFORMATION FOR SEQ ID NO:67:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:67:

```
Gly Cys Val Leu Leu Tyr Asp Glu Arg Thr Cys Gly
1               5                   10
```

(2) INFORMATION FOR SEQ ID NO:68:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:68:

```
Gly Cys Val Asp Leu Tyr His Tyr Val Tyr Cys Gly
1               5                   10
```